United States Patent [19]

Trevillyan

[11] 3,998,864
[45] Dec. 21, 1976

[54] HETEROGENEOUS CATALYST FOR THE HYDROFORMYLATION OF OLEFINS

[75] Inventor: Alvin E. Trevillyan, Naperville, Ill.

[73] Assignee: Standard Oil Company a corporation of Indiana, Chicago, Ill.

[22] Filed: Feb. 3, 1975

[21] Appl. No.: 546,323

[52] U.S. Cl. .................. 260/439 R; 252/431 P; 260/429 R; 260/604 HF; 260/606.5 P
[51] Int. Cl.² ................................ C07F 15/06
[58] Field of Search ........ 260/439 R, 2 M, 80 PS, 260/429 R, 606.5 P, 604 HF; 252/431 P

[56] References Cited
UNITED STATES PATENTS

| | | | |
|---|---|---|---|
| 3,270,087 | 8/1966 | Heck | 252/431 P |
| 3,792,099 | 2/1974 | Wang et al. | 260/668 R |
| 3,798,281 | 3/1974 | Wang | 260/668 R X |
| 3,824,221 | 7/1974 | Ragg | 260/80 PS |
| 3,855,332 | 12/1974 | Wang | 260/668 R X |

*Primary Examiner*—Helen M. S. Sneed
*Attorney, Agent, or Firm*—Gunar J. Blumberg; Arthur G. Gilkes; William T. McClain

[57] ABSTRACT

A novel, heterogeneous catalyst is useful in an improved process for the production of aldehydes and alcohols from olefinic hydrocarbons in the presence of carbon monoxide and hydrogen. The catalyst consists of a polyphenylene substrate to which are bonded diphenylphosphine ligands complexed with a metal carbonyl, such as cobalt carbonyl. The catalyst has excellent thermal stability, is essentially insoluble in the reactants or reaction products, and is active in the hydroformylation reaction at a temperature of about 195° C and a pressure of about 500 psig.

2 Claims, No Drawings

HETEROGENEOUS CATALYST FOR THE HYDROFORMYLATION OF OLEFINS

BACKGROUND OF THE INVENTION

The hydroformylation of olefins to yield aldehydes and alcohols is a well known reaction. Typically, olefins are reacted with carbon monoxide and hydrogen at a temperature of from about 100° to about 300° C and a pressure of from about 1,000 to about 4,500 psig in the presence of a soluble, homogeneous catalyst such as cobalt octacarbonyl. High reaction pressures are necessary with such prior art catalysts to prevent decomposition of the catalyst. To overcome this disadvantage, metal carbonyl catalysts have been complexed with certain ligands to provide catalysts that are more stable and are effective at pressures as low as one atmosphere. Thus, for example, U.S. Pat. No. 3,239,569 discloses that cobalt carbonyl can be complexed with stabilizing phosphorus-containing ligands such as trialkylphosphines to yield catalysts that are highly effective at low pressures. Also, U.S. Pat. No. 3,239,566 discloses catalysts that are stable and active at low pressures consisting of ruthenium or rhodium in complex combination with carbon monoxide and trialkylphosphines. All of these catalysts, however, suffer from the disadvantage that they are soluble, so that time consuming and costly catalyst separation and recovery steps must be employed.

Several heterogeneous hydroformylation catalysts have been disclosed in an attempt to avoid the problems of catalyst separation and recovery. U.S. Pat. No. 3,487,112, for example, teaches the preparation of a ruthenium carbonyl catalyst complexed with an alkylphosphine, or an alkylarsine, supported on alumina or carbon. Netherlands Patent No. 70/16532 discloses silica or silica-alumina as a support for hydroformylation catalysts. And Netherlands Patent No. 70/06740 discloses polystyrene and polyvinyl chloride as catalysts supports. Still other heterogeneous catalysts are disclosed in German Patent No. 2,000,829 and Netherlands Patent No. 70/18322. Some of the above-cited catalysts involve a reversible adsorption of the metal carbonyl catalyst on an amorphous solid; others involve the incorporation of the catalyst ligand into a polymer backbone. In the first instance, the catalyst is easily leached away from the support by hydroformylation reactants and reaction products; in the second instance, conventional polymers such as polystyrene and polyvinyl chloride are partially soluble in the reaction mixture and in addition have poor thermal stability at the elevated temperatures required for hydroformylation.

SUMMARY OF THE INVENTION

This invention relates to a novel, heterogeneous catalyst that is useful in an improved process for the production of aldehydes and alcohols from olefinic hydrocarbons in the presence of carbon monoxide and hydrogen. The catalyst is prepared from a polyarylene substrate having a number average molecular weight in the range of about 1,000 to about 10,000, preferably a number average molecular weight in the range of about 1,000 to about 3,000. Diaryl or dialkyl phosphine groups are bonded to the polymer substrate chain and these groups are used as ligands to complex metal carbonyls such as cobalt, rhodium, ruthenium, osmium, iridium, and iron carbonyls.

The amount of phosphorus incorporated into the polymer is dependent on the balance between maximizing catalytic activity and minimizing changes in the desirable insolubility and high thermal stability of the polymer. A suitable balance is achieved by incorporating phosphine groups in the polymer in amounts such that the ratio of aryl groups in the polymer to phosphorus atoms is in the range of about 1 to about 20, preferably in the range of about 5 to about 10.

Similarly, the amount of metal carbonyl to incorporate into the final catalyst depends on the balance between maximum catalytic activity per unit weight of catalyst and the possibility of metal loss from the catalyst. It is generally desirable to have an excess of phosphine groups relative to metal atoms so that if some metal carbonyl is lost by dissociation, there are ample phosphine sites available to re-complex the metal carbonyl from solution. Thus, a suitable ratio of phosphorus atoms to metal atoms is in the range of from about 1 to about 20, preferably in the range of about 2 to about 10.

The catalyst prepared as described above has the advantages over prior art catalyst in that it is completely heterogeneous: it does not exhibit even partial solubility nor does it swell on exposure to reactants or products in the hydroformylation reaction. Furthermore, the catalyst is more thermally stable than prior art catalysts prepared, for example, with a polystyrene or polyvinyl chloride substrate. And the polyarylene substrate employed in the preparation of the catalyst is, of itself, catalytically inert and does not catalyze undesirable side reactions.

The catalyst of this invention, being completely heterogeneous, provides an improved hydroformylation process in that costly catalyst separation and recovery steps are eliminated. The catalyst can be employed in the production of aldehydes and alcohols by contacting an olefinic hydrocarbon with carbon monoxide and hydrogen under conditions well known for the hydroformylation reaction. Typically, reaction conditions comprising temperatures in the range of about 100° to about 300° C and pressures in the range of about 10 to about 2,000 psig are utilized.

The amount of catalyst to be used in the reaction is not critical and may vary over a wide range; for example, olefin to catalyst weight ratios between 500:1 and 1:1 are suitable. Particularly suitable are olefin to catalyst weight ratios ranging from about 20:1 to about 5:1.

Olefins containing 4 to 19 carbon atoms, particularly those containing 6 to 10 carbon atoms are feedstocks that can be utilized advantageously. Under the conditions of the hydroformylation reaction, the olefins are converted to aldehydes and alcohols having one more carbon atom than the olefin charged.

The mole ratios of hydrogen to carbon monoxide employed may vary widely, for example, over the range of about 1:1 to about 10:1. The specific ratio to be used will be governed in part by the nature of the reaction products desired. For example, if an aldehyde product is desired, a suitable mole ratio of hydrogen to carbon monoxide is 1; if an alochol is the desired product, a suitable mole ratio is 2.

The liquid reaction products are readily separated from the catalyst by decantation or filtration and may be purified by distillation or other conventional means.

DESCRIPTION OF THE PREFERRED EMBODIMENTS

The polyarylenes utilized in the preparation of the catalysts of this invention are disclosed in U.S. Pat. Nos. 3,792,099; 3,798,281; and 3,855,332 which are incorporated herein by reference. The polyarylenes are prepared, for example, by treating an aromatic hydrocarbon with hydrogen in the presence of an $Al_2O_3$—$SiO_2$—$MoO_3$ catalyst system at a temperature of at least 800° F and a pressure of at least 600 psig. A particularly useful polyarylene is polyphenylene prepared as disclosed in U.S. Pat. No. 3,798,281 by reacting biphenyl and hydrogen in the presence of an $Al_2O_3$—$SiO_2$ catalyst impregnated with 2% $MoO_3$. The reaction is carried out in a stirred autoclave for 6 hours at a peak temperature of 1,085° F and a maximum pressure of 1,700 psig. After the polymerization is concluded, the crude product is dissolved in 1,2,4-trichlorobenzene and filtered to remove catalyst. The polymer is precipitated out by addition of n-pentane, filtered, and washed with n-pentane. The polymer is then dried at 100° C for 24 hours. The polymer is a branched polyphenylene comprising benzene ring structures bonded into a polymer chain wherein the amount of benzene ring structures bonded to three or more other benzene ring structures is from 15 to 25% by weight, the amount of benzene ring structures bonded to two other benzene ring structures is from 45 to 65% by weight, and the amount of benzene ring structures bonded through the meta position to two other benzene ring structures is from 15 to 30% by weight, with the remaining benzene ring structures being bonded to only one other benzene ring structure. The catalyst was prepared by the reactions depicted schematically as follows:

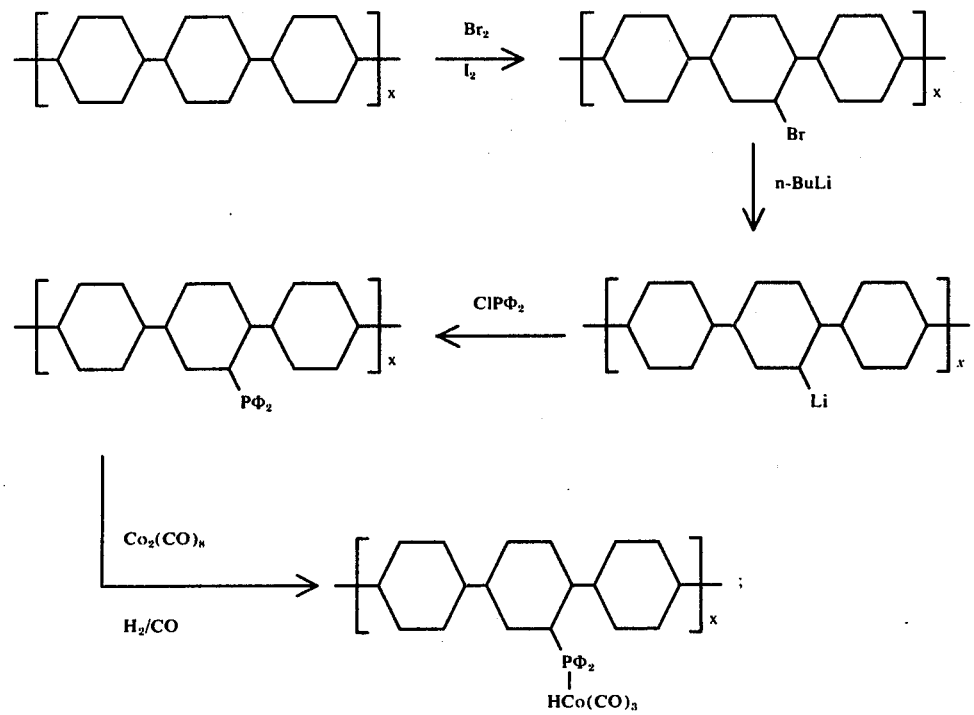

where $\phi$ is phenyl and $x$ is a set of values such that the molecular weight of the polymer backbone ranges from about 1,000 to about 10,000.

EXAMPLE I

Ten grams of polyphenylene prepared in the above-described manner and having a number average molecular weight of 2,000 was placed in a 500 ml fluted flask fitted with a stirrer, drop funnel, reflux condenser, and thermometer. One hundred-fifty ml 1,2,4-trichlorobenzene was added and the mixture was stirred to dissolve the polymer. A small amount, 0.1 g, of iodine was added to the flask and then 4.2 g bromine was added dropwise through the dropping funnel over a 10 minute period. The resulting solution was heated to 60° C for 1 hour and then stirred overnight at room temperature. The mixture was dissolved in $CH_2Cl_2$ and extracted with 100 ml of 10% aqueous NaOH. The $CH_2Cl_2$ was evaporated off and the residue was poured into 500 ml n-pentane. After drying, 8.5 g of brown solid was obtained which contained 16.3 weight percent bromine.

The brominated polymer was dissolved in 1,000 ml of dry benzene in a two liter flask fitted with a stirrer, reflux condenser, vapor by-pass addition funnel, and an inlet for an inert gas. An atmosphere of argon was maintained throughout the reaction. Twenty grams of 21.5 weight percent solution of n-butyl lithium in n-hexane was added over a 30 minute period. The mixture was heated to 35°–40° C for 1.5 hours with stirring, and then stirred overnight at room temperature. Fifteen grams of diphenylchlorophosphine was then added to the reaction mixture and this was stirred at room temperature for 1 hour, and at 35°–40° C for 30 minutes. The mixture was dissolved in 2,500 ml of $CH_2Cl_2$ and washed once with 100 ml water. The solution was dried over anhydrous $MgSo_4$, the $CH_2Cl_2$ evaporated, and the residue poured into two liters of n-heptane to precipitate the phosphinated polymer. The solid was removed by filtration, washed with fresh heptane, and dried under vacuum at room temperature. The brown solid weighed 6.7g and contained 1.92% bromine and 4.36% phosphorus. It was stored under a dry nitrogen atmosphere.

In a one liter autoclave were placed 320 g heptane, 6.7 g of the phosphinated polymer prepared above, and 0.5 g of dicobalt octacarbonyl. The autoclave was sealed and pressured to 200 psig with a $H_2/CO$ mixture having a mole ratio of 2:1. The contents were stirred at 2,000 rpm and heated to 195° C, whereupon the pressure rose to 400 psig. These reaction conditions were maintained for two hours.

To the catalyst mixture prepared above was added 67.2 g (.60 mole) of octene-1 and 40 g of n-decane (employed as an internal standard for gas chromatography analysis). The reaction mixture in the autoclave was heated to 195° C and the pressure was increased to 500 psig with a $H_2/CO$ mixture having a mole ratio of 2:1. These conditions were maintained for 2.5 hours. Another 0.5 g of dicobalt octacarbonyl was added and the reaction continued for 6 hours. The reactor was then cooled and the reaction mixture was then filtered to separate the catalyst from the liquid product.

The recovered catalyst contained 1.09 weight percent cobalt and 4.21 weight percent phosphorus. The ratio of phenyl groups to phosphorus atoms was 7.0 and the ratio of phosphorus atoms to cobalt atoms was 7.4.

Analysis of the liquid reaction mixture is given in the following table:

| | | |
|---|---|---|
| n-Octenes | 47.9 g | (.428 mole) |
| n-Octane | 3.3 g | (.0293 mole) |
| $C_9$ Aldehydes | 11.2 g | (.0789 mole) |
| $C_9$ Alcohols | 4.5 g | (.0315 mole) |
| | (.568 mole) | |
| chain material in aldehyde and alcohol product | 38% | |
| Cobalt | <5 ppm | |

Based on these data the hydroformylation reaction may be summarized as follows:

| | |
|---|---|
| Material Balance | 95 mole % |
| Conversion of Octenes | 29 mole % |
| Selectivities: | |
| To Octane | 17 mole % |
| To $C_9$ Aldehydes | 46 mole % |
| To $C_9$ Alcohols | 18 mole % |
| | 81 mole % |

The data tabulated above indicate that the catalyst of this invention is active for the hydroformylation reaction, as evidenced by the formation of aldehyde and alcohol; and is heterogeneous, as evidenced by the extremely low amount of cobalt in the liquid product.

The sequence of reactions above is given by way of illustration only. Other preparative methods to obtain the desired catalyst composition can be employed and will be evident to those skilled in the art.

I claim:

1. A composition which comprises a polyphenylene containing benzene ring structures bonded into a polymer chain wherein the amount of benzene ring structures bonded to three or more other benzene ring structures is from 15 to 25% by weight, the amount of benzene ring structures bonded to two other benzene ring structures is from 45 to 65% by weight, and the amount of benzene ring structures bonded through the meta position to two other benzene ring structures is from 15 to 30% by weight, with the remaining benzene ring structures being bonded to only one other benzene ring structure, said polyphenylene having a number average molecular weight in the range of about 1000 to about 10000, said polyphenylene having $-PR_2$ substituents, where R is a phenyl or alkyl group, in amounts such that the ratio of phenyl groups to phosphorus atoms is in the range of about 1.0 to about 20, said $-PR_2$ groups being complexed with a metal carbonyl compound selected from the group consisting of cobalt, rhodium, ruthinium, osmium, irridium, and iron carbonyls in amounts such that the ratio of phosphorus atoms to metal atoms is in the range of from about 1 to about 20.

2. The composition of claim 1 wherein the number average molecular weight of the polyphenylene is in the range of from about 1,000 to about 3,000, the R groups in $-PR_2$ are phenyl, the ratio of aryl groups to phosphorus atoms is in the range of about 5 to about 10, the complexing metal carbonyl compound is cobalt carbonyl, and the ratio of phosphorus atoms to cobalt atoms is in the range of from about 2 to about 10.

* * * * *

UNITED STATES PATENT OFFICE
CERTIFICATE OF CORRECTION

Patent No. 3,998,864　　　　　　　　　　Dated　December 21, 1976

Inventor(s) Alvin E. Trevillyan

It is certified that error appears in the above-identified patent and that said Letters Patent are hereby corrected as shown below:

Column 5, line 35, "Total" should be indicated between the 1st & 2nd columns;

(.568 mole) should appear in last column instead of 2nd.

"　　　line 36, "Straight" should precede "chain material."

Signed and Sealed this

Tenth Day of May 1977

[SEAL]

Attest:

RUTH C. MASON  
Attesting Officer

C. MARSHALL DANN  
Commissioner of Patents and Trademarks